US 6,447,787 B1

(12) United States Patent
Gassner et al.

(10) Patent No.: US 6,447,787 B1
(45) Date of Patent: Sep. 10, 2002

(54) METHODS FOR ENHANCING WOUND HEALING

(75) Inventors: Holger G. Gassner, Erlangen (DE); David A. Sherris, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 09/807,793

(22) PCT Filed: Oct. 15, 1999

(86) PCT No.: PCT/US99/24182

§ 371 (c)(1),
(2), (4) Date: Apr. 18, 2001

(87) PCT Pub. No.: WO00/24419

PCT Pub. Date: May 4, 2000

Related U.S. Application Data

(60) Provisional application No. 60/105,688, filed on Oct. 27, 1998.

(51) Int. Cl.[7] .......................... A61K 39/08; A61K 39/02
(52) U.S. Cl. ............................. 424/247.1; 424/239.1; 424/236.1
(58) Field of Search ............................ 424/247.1, 239.1, 424/236.1

(56) References Cited

U.S. PATENT DOCUMENTS

| | | |
|---|---|---|
| 3,957,996 A | 5/1976 | Adams et al. ............... 424/253 |
| 3,966,934 A | 6/1976 | Adams et al. ............... 424/251 |
| 4,029,793 A | 6/1977 | Adams et al. |
| 4,029,794 A | 6/1977 | Adams et al. |
| 4,080,448 A | 3/1978 | Mirsky |

FOREIGN PATENT DOCUMENTS

| | | |
|---|---|---|
| EP | 0 845 267 A1 | 6/1998 |
| JP | 55 094319 | 7/1980 |
| WO | WO 94/28923 | 12/1994 |
| WO | WO 98/43619 | 10/1998 |

OTHER PUBLICATIONS

Adler et al., "Brief Report—Perioperative Use of Botulinum Toxin for Movement Disorder–Induced Cervical Spine Disease," *Mov. Disord.*, 1996, 11:79–81.

Armstrong et al., "Treatment of facial synkinesis and facial asymmetry with botulinum toxin type A following facial nerve palsy," *Clin. Otolaryngol.*, 1996, 21:15–20.

Borges, *Elective Incisions and Scar Revision*, 1973, Little, Brown and Company Inc., Boston, p. 29.

Carruthers et al., "Botulinum A exotoxin use in clinical dermatology," *J. Am. Acad. Dermatol.*, 1996, 34(No. 5, Part 1):788–797.

Childers, "Myofascial Pain Syndromes," *Use of Botulinum Toxin Type A in Pain Management*, 1999, Academic Information Systems, Columbia, MO, Chapter 5, pp. 30–50.

Courtiss et al., "The Placement of Elective Skin Incisions," *Plast. Reconstr. Surg.*, 1963, 31:31–44.

(List continued on next page.)

*Primary Examiner*—Frederick Krass
*Assistant Examiner*—Donna Jagoe
(74) *Attorney, Agent, or Firm*—Fish & Richardson, P.C., P.A.

(57) ABSTRACT

A method for treating a patient having a wound is described. The method includes administering an amount of a chemodenervating agent such that healing of the wound is enhanced. The method is illustrated by detailing the mean differences of the scores of the paired experimental and control scars across three observers.

34 Claims, 1 Drawing Sheet

OTHER PUBLICATIONS

Dreyer, "Peripheral Actions of Tetanus Toxin," *Botulinum Neurotoxin and Tetanus Toxin*, 1989, Simpson (ed.), Academic Press, Inc., San Diego, pp. 179–202.

Foster et al., "The Use of Botulinum A Toxin to Ameliorate Facial Kinetic Frown Lines," *Ophthalmology*, 1996, 103(4):618–622.

Gasser et al., "Botulinum toxin A in orthopaedic surgery," *Lancet*, 1991, 338:761.

Gassner et al., "Treatment of Facial Wounds with Botulinum Toxin A Improves Cosmetic Outcome in Primates," *Plast. Reconstr. Surg.*, 2000, 105(6):1948–1953.

Gassner and Sherris, "Addition of an Anesthetic Agent to Enhance the Predictability of the Effects of Botulinum Toxin Type A Injections: A Randomized Controlled Study," *Mayo Clin. Proc.*, 2000, 75(7):701–704.

Greene and Fahn, "Response to Botulinum Toxin F in Seronegative Botulinum Toxin A–Resistant Patients," *Mov. Disord.*, 1996, 11(2):181–184.

Habermann et al., "Tetanus Toxin Blocks the Neuromuscular Transmission in vitro Like Botulinum A Toxin," *Naunyn–Schmiedeberg's Arch. Pharmacol.*, 1980, 311:33–40.

Magoon et al., "Diagnostic Injection of Xylocaine into Extraocular Muscles," *Ophthalmology*, 1982, 89(5):489–491.

Maria et al., "A Comparison of Botulinum Toxin and Saline for the Treatment of Chronic Anal Fissure," *N. Engl. J. Med.*, 1998, 338(4):217–220.

Matsuda et al., "Acute Botulinum–Like Intoxication by Tetanus Neurotoxin in Mice," *Biochem. Biophys. Res. Commun.*, 1982, 104(2):799–805.

McCarthy, *Plastic Surgery*, 1990, vol. 1, WB Saunders, Philadelphia, pp. 43–44, 49.

McKellar and Lorentz, "The Use of Botulinum Toxin in the Treatment of Oro–Mandibular Dystonias and Fractures of the Mandibular Condyle," *Mov. Disord.*, 1992, 7(Suppl. 1):134.

Morré et al., "Treatment of chronic tennis elbow with botulinum toxin," *Lancet*, 1997, 349(9067):1746.

Racette et al., "Preoperative treatment with botulinum toxin to facilitate cervical fusion in dystonic cerebral palsy," *J. Neurosurg.*, 1998, 88:328–330.

Robinson, "Purification of Tetanus Toxin and Its Major Peptides," *Methods Enzymol.*, 1988, 165:85–90.

Rubin, "Langers Lines and Facial Scars," Read before the American College of Surgeons, Kings County Hospital, Brooklyn, N.Y., Sep. 10, 1947, pp. 147–155.

Schantz et al., "The Structure of Saxitoxin," *J. Am. Chem. Soc.*, 1975, 97:1238–1239.

Schantz and Johnson, "Properties and Use of Botulinum Toxin and Other Microbial Neurotoxins in Medicine," *Microbiol. Rev.*, 1992, 56:80–99.

Schantz and Johnson, "Botulinum Toxin: the Story of its Development for the Treatment of Human Disease," *Perspective in Biology and Medicine*, 1997, 40(4):317–327.

Scott and Suzuki, "Systemic Toxicity of Botulinum Toxin by Intramuscular Injection in the Monkey," *Mov. Disord.*, 1988, 3(4):333–335.

Sherris et al., "Management of Scar Contractures, Hypertrophic Scars, and Keloids," *Otolaryngologic Clinics of North America*, 1995, 28(5):1057–1068.

Simon et al., "Lacerations Against Langer's Lines: to Glue or Suture?" *J. Emergency Med.*, 1998, 16(2):185–189.

Traynelis et al., "Botulinum toxin enhancement of postoperative immobilization in patients with cervical dystonia," *J. Neurosurg.*, 1992, 77:808–809.

Truong et al., "Brief Report—BotB (Botulinum Toxin Type B): Evaluation of Safety and Tolerability in Botulinum Toxin Type A–Resistant Cervical Dystonia Patients (Preliminary Study)," *Mov. Disord.*, 1997, 12(5):772–775.

Wheeler, "Therapeutic Uses of Botulinum Toxin," *Am. Family Physician*, 1997, 55(2):541–545.

Yotsu et al., "Production of Tetrodotoxin and its Derivatives by Pseudomonas SP. Isolated from the Skin of a Pufferfish," *Toxicon*, 1987, 25(2):225–228.

McKellar and Lorentz, "The Use of Botulinum Toxin in the Treatment of Oro–Mandibular Dystonias and Fractures of the Mandibular Condyle," *Australian and New Zealand Journal of Medicine*, 1992, 22(4):428 –XP–001057090.

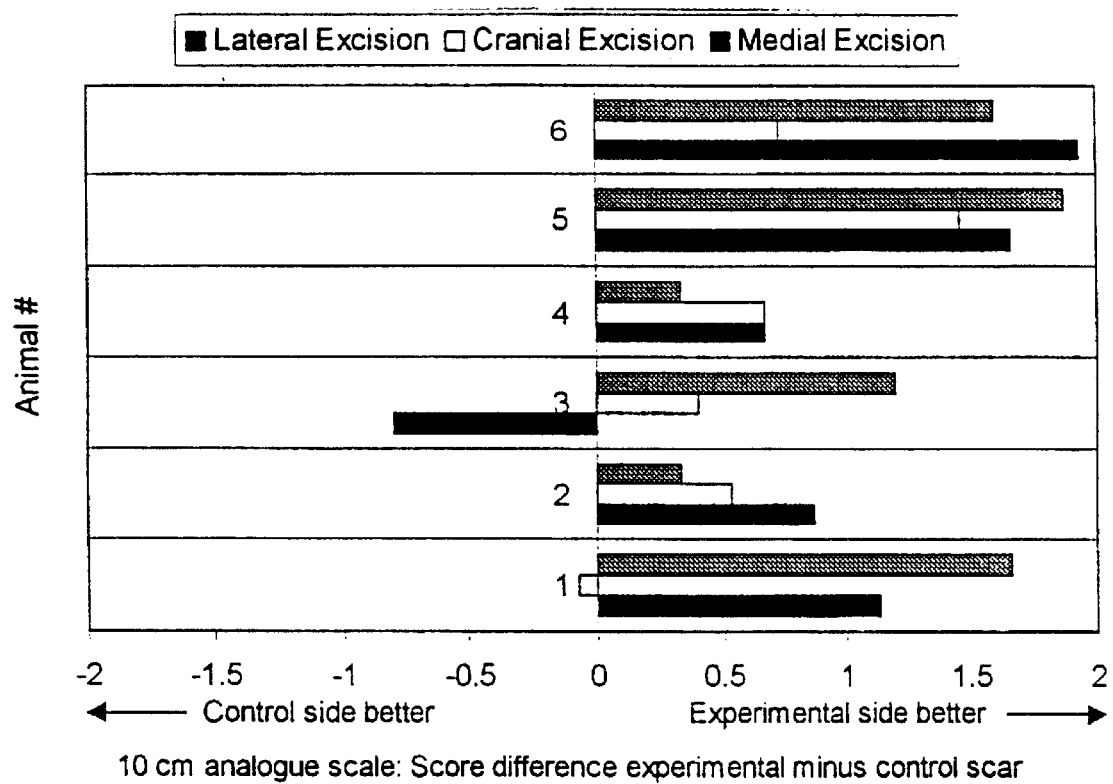

METHODS FOR ENHANCING WOUND HEALING

This application is the national stage (371) of PCT/US99/24182 filed Oct. 15, 1999 which claims the benefit of provisional application No. 60/105,688 filed Oct. 27, 1998.

TECHNICAL FIELD

The invention relates to a method for enhancing wound healing.

BACKGROUND OF THE INVENTION

Immobilization is a basic therapeutic principle in wound healing, common to the treatment of lesions of all kinds. Casts, plates, and sutures minimize the negative effects of muscle tension on healing tissues. Since tension is one of the chief factors determining the degree of scar formation, this principle also holds true in skin lesions. The carefully-planned execution of an elective skin incision frequently achieves the best aesthetic result.

Surgeons have been seeking techniques and methods to reduce excessive scar formation, especially in the face. Many approaches have been undertaken to overcome the negative influence of muscular tension on the wound healing process, including various suture techniques, steroid injections, undermining wound edges, and placing incisions in a line parallel to relaxed skin tension lines (RSTLs).

The etiology of skin tension lines, first described more than a century ago, has been subject to controversy over the years. There is general agreement, however, that skin tension lines influence the healing of incisions according to their relative positions. There is evidence that the formation of RSTLs is a dynamic process over time. Studies on fetal calves and human fetal skin suggest that RSTLs are not genetically determined, but represent a change of texture of the skin secondary to extrinsic and/or intrinsic forces. Lorenz, H. P. et al., *Development*, 114(1):253–259, (1992). This change in texture gives skin certain mechanical characteristics that are retained even when excised. Muscle tension is thought to be a major factor in the formation of RSTLs.

Increased skin tension has a negative effect on wound healing, causing hypertrophic scars or wound dehiscence. See, for example, Sherris, D. A. et al., *Otolaryngologic Clinics of North America*, 28(5): 1957–1968, 1995. Repeated microtrauma, caused by continuous displacement of injured tissue, induces a prolonged inflammatory response and an increased metabolic activity during the healing process. As a consequence, extracellular deposition of collagen and glycosaminoglycans can intensify and lead to hypertrophic scars. The incidence of hypertrophic scars is higher in certain anatomic areas where there is increased muscular movement. McCarthy, J. G., Plastic Surgery, 1990, Vol. 1, Philadelphia, W B Saunders, page 44.

SUMMARY OF THE INVENTION

The invention is based, in part, on a new therapy for management of both traumatic and iatrogenic wounds, which includes the elimination of the tension acting on the wound. The new therapy includes injection of a chemodenervating agent to paralyze muscles capable of exerting tension on such wounds, providing better wound healing with minimal scar development. In addition, early immobilization in elective procedures also allows a surgeon to use finer sutures, further improving the cosmetic result.

In one aspect, the invention features a method for treating a patient having a wound (e.g., a facial wound). The method includes locally administering an amount of a chemodenervating agent such that healing of the wound is enhanced. The chemodenervating agent can be, for example, a botulinum toxin, saxitoxin, tetanus toxin, or tetrodotoxin, and is typically administered by injection. The botulinum toxin can be botulinum toxin A, B, C, D, E, F, or G, and in particular botulinum toxin A or B. The method further can include administering an amount of a local anesthetic agent and/or a local vasoconstrictive agent effective to enhance wound healing. Local anesthetic agents such as lidocaine, bupivacaine, or mepivacaine, or local vasoconstrictive agents can be administered prior to injection with the chemodenervating agent or simultaneously with the chemodenervating agent.

A composition having a chemodenervating agent, a local anesthetic, and a local vasoconstrictive agent also is featured.

In another aspect, the invention features an article of manufacture that includes packaging material and an amount of a chemodenervating agent. The packaging material includes a label that indicates the chemodenervating agent is useful for treating a patient having a wound. Administration of the chemodenervating agent enhances healing of the wound. The chemodenervating agent can be a botulinum toxin such as botulinum toxin A. The article of manufacture also can include a local anesthetic agent or a vasoconstrictive agent.

Unless otherwise defined, all technical and scientific terms used herein have the same meaning as commonly understood by one of ordinary skill in the art to which this invention belongs. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE DRAWINGS

FIG. 1 is a graph that indicates the mean differences of the scores of the paired experimental and control scars across three observers.

DETAILED DESCRIPTION

As described herein, the cosmetic appearance of a scar is influenced by underlying muscle activity during the wound healing process. Paralysis of the underlying muscle activity increases the rate of healing and yields a better cosmetic result. Without being bound by a particular mechanism, locally induced paralysis of the musculature subjacent to a cutaneous defect is thought to minimize the repetitive tensile forces on the wound edges, resulting in superior cosmetic outcome in the resultant scar.

Thus, the invention provides a method for treating a patient having a wound that includes locally administering an amount of a chemodenervating agent effective to enhance wound healing in the patient. As used herein, "chemodenervating agent" refers to any agent that interrupts nerve impulse transmission across the neuromuscular junction, blocks the release of neurotransmitters, or alters the action potential at the voltage gated sodium channel of neurons, sufficient to reduce tension within muscles in and near a wound site.

As used herein, "wound" refers to skin, tendon, or bone wounds, and can include inflammatory lesions or other lesions adversely affected by muscle tension or movement. Skin wounds include, for example, facial lacerations such as those introduced by trauma (i.e., a car accident), or iatrogenic, such as surgically introduced incisions. In particular, surgically introduced incisions include scar revision excision surgery. As such, a skin wound includes elective incisions and nonelective incisions. Skin wounds may be relatively favorable or unfavorable. As used herein, "favorable wound" refers to an incision or laceration that is relatively parallel to RSTLs, whereas "unfavorable wound" refers to an incision relatively perpendicular to RSTLs. Both favorable and unfavorable wounds benefit from the methods described herein. Tendon wounds include, for example, ruptured or injured tendons and tendinitis.

Bone wounds include favorable and unfavorable fractures. A "favorable fracture" refers to a fracture that is not prone to displacement of one or more fragments of the fracture by muscle pull, whereas an "unfavorable fracture" refers to a fracture that is prone to displacement of one or more fragments by muscle pull. The treatment for a fracture can be facilitated if muscle tension on the affected fracture is minimized. Thus, the treatment becomes less invasive, less time consuming and/or less costly. For example, with a fractured elbow, the triceps muscle can displace the bone fragments. An alternative to surgical repair includes use of percutaneous wires to hold the bones in place, and relaxation of the triceps muscle by paralysis with a chemodenervating agent. Use of wires and a chemodenervating agent may reduce or avoid surgery and/or the accompanying general anesthesia.

The methods described herein enhance wound healing by minimizing the adverse effect of muscle tension and movement on the wound, as well as improving cosmetic appearance through reduced scar development. In addition, inflammation may be reduced during the healing process.

Chemodenervating Agents

Non-limiting examples of chemodenervating agents include botulinum toxin, saxitoxin, tetanus toxin, and tetrodotoxin. Suitable botulinum toxins include, for example, botulinum toxins A, B, C (C1 and C2), D, E, F, or G. Botulinum toxins A, B, and F are particularly useful. Botulinum toxin A is a potent drug that produces temporary muscular paralysis when injected locally. Botulinum toxin A has been used in the treatment of a wide range of disorders associated with involuntary muscle contraction. It has been demonstrated to be effective in treating focal dystonias such as blepharospasm, nondystonic disorders such as hemifacial spasms, disorders of conjugate eye movement such as strabismus and nystagmus, spasticity disorders such as multiple sclerosis and cerebral palsy, and for disorders of localized muscle spasm. In addition, botulinum toxin A has been used to treat age related rhytids of the upper face. Botulinum toxin A is safe and effective to use, and is relatively painless with rare side effects characterized as mild and transient. Onset of action takes place within 24 to 72 hours after injection and lasts 2 to 6 months. Botulinum toxin A is available commercially, e.g. from Allergan, Inc. (Irvine, Calif. Botox®) and Speywood Pharmaceuticals (England, Dysport®).

Dosages of botulinum toxin A required for local immobilization typically do not exceed 1 unit toxin per kg body weight and are safe. Primate studies have indicated that no systemic effects are observed at dosages below 33 units/kg body weight. See, for example, Scott and Suzuki, *Mov. Disord*., 1988, 3:333–335.

Botulinum toxins B and F also have been used for dystonia patients. Greene, P. E. et al., *Mov. Disord*., 1996, 11(2):181–184; and Truong, D. D. et al., *Mov. Disord*., 1997, 12(5):772–775. Botulinum toxin B is available from Elan Corporation (Dublin, Ireland, Neurobloc®).

Botulinum toxins also can be obtained by purifying the toxins from strains of *Clostridium botulinum*, using standard techniques. For example, botulinum toxin A can be produced in a Hall strain using a nutritive medium containing casein digest, yeast extract, and dextrose. After lysis of the culture, the toxin is released into the medium and activated by proteases, and then is acid precipitated. Further purification can include extraction with a sodium phosphate buffer, ethanol precipitation, and crystallization in ammonium sulfate. See, for example, Schantz, E. J. and Johnson, E. A., *Microbiol. Rev*., 1992, 56(1):80–99.

Other chemodenervating agents such as saxitoxin, tetanus toxin, and tetrodotoxin are also suitable. The paralysis induced by saxitoxin, however, does not last as long as that induced by botulinum toxin. Consequently, repeated injections of saxitoxin may be needed. Saxitoxin can be purified by known procedures. See, for example, Schantz, E. J. et al., *J. Am. Chem. Soc*., 1975, 97:1238–1239. Tetanus toxin can decrease acetylcholine release in cholinergic peripheral nerves when injected locally. Dreyer, F., Peripheral actions of tetanus toxin, p. 179–202, In: Botulinum neurotoxin and tetanus toxin. Academic Press, Inc., San Diego. L. L. Simpson (ed.). Tetanus toxin also can enter the central nervous system where it causes uncontrolled muscle spasms. When tetanus toxin is employed in the methods described herein, precautions must be taken to ensure local response. Matsuda, M. et al., *Biochem. Biophys Res. Commun*., 1982, 104:799–805; and Habermann, E. et al., *Naunyn-Schmiedeberg's Arch. Pharmacol*., 1980, 311:33–40. Tetanus toxin can be purified by standard procedures. See, for example, Robinson, J. P., *Methods Enzymol*., 1988, 165:85–90. Tetrodotoxin blocks the sodium channel of excitable membranes of nerve and muscle tissues, and can be purified using routine techniques. See, for example, Yotsu, M. et al., *Toxicon*, 1987, 25:225–228.

Local administration of the chemodenervating agents typically occurs by subcutaneous (SQ), intramuscular (IM), perimuscular injection, or percutaneous instillation (e.g., air gun or skin patch). When chemodenervating agents are injected SQ, the agent reaches the muscle by perfusion. For elective incisions, the chemodenervating agent can be administered prior to making an incision, while making an incision, or after an incision has been made.

Administration of Local Anesthetics and Local Vasoconstrictive Agents

The method of treatment further can include administering either a local anesthetic agent or a local vasoconstrictive agent, or both. Such agents can be administered prior to injection of the chemodenervating agent or simultaneously with the injection of the chemodenervating agent. Local anesthetics block nerve conduction, and can cause sensory and motor paralysis in localized area. Local anesthetics have a rapid onset of action, and therefore reduce muscle tension on the wound almost immediately as well as reduce pain associated with the injection. The extent of muscular paralysis achieved by a local anesthetic agent is helpful in predicting the extent of paralysis that can be achieved by subsequent injection of a chemodenervating agent into the same injection site. Thus, possible local side effects, such as diffusion of the chemodenervating agent to adjacent muscle groups, is prevented. Non-limiting examples of local anesthetic agents include lidocaine, bupivacaine, chloroporcaine etidocaine, or mepivacaine, and are available commercially. In addition, other amide types of local anesthetics can be used in the method. Suitable amounts of local anesthetics can be readily determined by a physician. For example, about 1 to 5 mls of lidocaine at a concentration of about 0.5%–about 2% can be injected. Administration of local anesthetics is particularly useful when incisions are introduced surgically, such as during scar reversion excision surgery.

Administration of a local vasoconstrictive agent results in a decreased hemoperfusion of the injected tissue. Thus, administration of a local vasoconstrictive agent can help prevent or control diffusion of the chemodenervating agent and minimize possible side effects, such as brow ptosis or incomplete eye closure from injection into the frontalis and/or corrugator supercilii muscles. Non-limiting examples of local vasoconstrictive agents include epinephrine and phenylephrine, and are available commercially. A suitable amount of a local vasoconstrictive agent can be readily determined by a physician. For example, 5 mls of epinephrine 1:100,000 or 1:200,000 typically is used for local vasoconstrictive action.

Compositions containing a chemodenervating agent and a local anesthetic, and/or a local vasoconstrictive agent, can be produced for applications in which it is desired to introduce chemodenervating agents and one or more other components simultaneously. Such compositions can be prepared, for example, by reconstituting a lyophilized component with a solution of another component. For example, lyophilized botulinum toxin can be reconstituted in a solution containing a local anesthetic and a local vasoconstrictive agent, or in a solution containing either a local anesthetic or a local vasoconstrictive agent. A composition containing lidocaine and epinephrine is commercially available, for example, from Astra. Typically, lidocaine is present at 0.5–2% and epinephrine is present at 1:100,000 to 1:200,000.

The invention will be further described in the following examples, which do not limit the scope of the invention described in the claims.

EXAMPLE 1

Enhanced Wound Healing By Injection of a Chemodenervating Agent in Monkeys

In order to closely mimic the effects of muscle activity on human facial skin wounds, the use of an appropriate animal model was mandatory. Due to extensive skin laxity and inadequate mimetic musculature, established models like rats, pigs, and horses, were not ideal for this purpose. *Cynomolgus macaque* monkeys (*Macaca fascicularis*) were chosen as a model since the anatomy of their cranio facial and cutaneous anatomy resembles that of humans.

The study was approved by the Institutional Committee of Animal Care and Use at the Mayo Clinic and the animals were housed, cared for, and fed in compliance with the institutional guidelines. No animal was sacrificed. All procedures were performed with anesthesia consisting of Ketamine at 20 mg/kg IM (Ketaset®, Fort Dodge), Xylazine at 0.5 mg/kg IM (Rompun®, Bayer), and Isoflurane at 1% (Isoflurane®, Abbott).

The forehead was chosen for the excision site in the monkeys as the frontalis, procerus and corrugator supercilii muscles constantly exert tension on the forehead skin and paralysis of these muscles leads to no functional deficit. In order to minimize local variables, the experimental and control excisions were each planned in symmetric anatomic location in the same individual animal. Three Y-shaped excisions with their main axis perpendicular to the RSTLs were planned symmetrically in relation to the midline on each side of the forehead.

A template was used to determine the location and outline of the excisions to ensure maximal precision. An experienced facial plastic surgeon, blinded to the experimental conditions, performed all excisions. Using standard surgical technique, the skin and subcutaneous tissue was excised and the frontalis muscle was preserved in the base of the defects. Subsequently, one side of the forehead was randomly determined as experimental and the mimetic musculature adjacent to each excision on that side was injected under direct vision with 7 units of Botulinum Toxin A (Botox®, Allergan) in 0.9% saline (25 units/ml), resulting in a total dose of 21 units of Botulinum toxin A per half forehead. The control side was injected in the same fashion with an equal volume of 0.9% saline alone. All wounds were closed with a single 6-O Chromic Gut (Chromic Gut®, Ethicon) buried suture and multiple 5-O black monofilament Nylon (Ethilon®, Ethicon) superficial sutures. From the third day postoperatively, marked paralysis of the Botulinum toxin A treated side was observed in all six animals. Extraocular muscle movement and eyelid closure were not compromised.

Three experienced facial surgeons, who were not present during the surgical procedures, were used as blinded observers to evaluate the cosmetic appearance of the scars at 1, 4, and 12 weeks postoperatively. Care was taken to sedate the animals deeply for each assessment so the evaluators were not able to recognize the paralyzed side of the forehead.

First, the evaluators were asked to score each single scar on a 10 cm visual analogue scale. The 36 forehead scars (3 experimental scars and 3 control scars per animal) were evaluated by each assessor independently. In this scale, scars were rated from 1 to 10, with 0 being the worst and 10 being the best. At 1 and 4 weeks postoperatively, none of the blinded ratings revealed a significantly better cosmetic appearance of the experimental or the control wounds. The mean ratings of the three assessors at 12 weeks postoperatively reached a higher score on the experimental side in 16 of 18 of the symmetric pairs of scars (FIG. 1). The bars in FIG. 1 represent the mean differences of the scores of the paired experimental and control scars across the three observers. The mean score by assessor #1 was 9.4 for the experimental scars and 8.1 for the control scars; the mean score by assessor #2 was 8.0 for the experimental scars and 7.3 for the control scars; and the mean score by assessor #3 was 7.9 for the experimental scars and 7.3 for the control scars. The mean scores across the three assessors were 8.4 (SD 1.0) for the experimental side and 7.6 (SD 0.9) for the control side. The statistical assessment of an intervention effect was based on using the average rating across the three evaluators and fitting a two-factor (intervention, site) repeated measures analysis of variance model, taking into account the correlation of measurements obtained on the same animal. Based on this analysis, the scars on the experimental side were rated significantly better than the scars on the control side ($p<0.01$).

Secondly, the assessors were asked to examine the groups of 3 scars on either side of each animal's forehead (12 weeks postoperatively) and to rate each scar as better, equal to, or worse than its symmetric counterpart. A consensus score was derived from the majority of the votes. The experimental sides were assessed as better than the control sides in 6 of the 6 animals. Based on a two-tailed, one-sample binomial test, this result was statistically significant ($p<0.031$) (Table 1).

TABLE 1

Assessment of Scars

| Animal | Assessor 1 | Assessor 2 | Assessor 3 | Consensus Score |
|---|---|---|---|---|
| 1 | + | ? | + | + |
| 2 | + | ? | + | + |
| 3 | + | + | − | + |
| 4 | + | + | + | + |
| 5 | + | + | + | + |
| 6 | + | + | + | + |

+ = Assessment of experimental side as better
− = Assessment of experimental side as worse
? = Assessment of both sides equal Representative sections of the scars were excised 12 weeks postoperatively, using a 4 mm punch. The biopsy specimens were embedded in formalin, cut in 25 μm thick sections, and hematoxylin and Eosin stained for evaluation. Scars were classified as mature with no sign of inflammation or ongoing remodeling.

EXAMPLE 2

Enhanced Wound Healing by Botulinum Injection in Humans

A male patient (26 years of age, 82 kg) underwent scar revision excision surgery. The scar was located on the forehead approximately 2 cm lateral of the midline on the left, and approximately 3 cm cranial to the most superior extension of the orbital rim. Its direction was horizontal, giving it a favorable position relative to the wrinkle lines. The scar was a result of a trauma at age seven, and was closed at a tertiary referral center at the time.

The patient was placed in a supine position, and 5 ml of 0.5% lidocaine with 1:200,000 epinephrine was locally injected. The scar was excised and bleeding was controlled with monopolar cautery. Botulinum toxin A was injected (10 units) into the frontalis muscle under direct vision fanning out from the wound. The wound was closed using 6-0 Vicryl for deep and 6-0 Nylon for superficial sutures. An additional 7.5 units of botulinum toxin A were injected into the procerus and corrugator muscles bilaterally, as frowning caused distortion of the wound.

Approximately 24 hours after surgery, the patient developed marked paralysis of the injection muscles, and had lost the ability to wrinkle the forehead skin in an area of about 4 cm in diameter around the excision. The wound healed well in the early postoperative period. It was apparent that there was decreased movement and tension on the wound edges. The forehead wound of the patient healed without complications. Compared to the preoperative scar, the cosmetic appearance of the resulting scar 12 months postoperatively was excellent and superior to the initial scar.

EXAMPLE 3

Evaluation of Scars from Patients Injected with a Chemodenervating Agent Alone or in Combination with a Local Anesthetic Healthy volunteers were informed about potential risks and side effects of the treatment. Formal written informed consent was obtained in accordance with the Mayo Institutional Review Board regulations. Prior to enrollment in the study, symmetry of frontalis, procerus, and corrugator supercilii function was assessed and subjects were only included in the study if there was no functional asymmetry present. The forehead of the subjects was divided by the midline into two symmetric sides, one serving as the control and the other as the experiment side. The side of the forehead which was to serve as control was determined randomly, and was injected with Botulinum Toxin A (Botox) reconstituted in 0.9% saline. The experimental side was injected with Botulinum Toxin A reconstituted in 1% or 2% lidocaine with 1:100,000 epinephrine. The combination of these agents with Botulinum toxin A was achieved by reconstituting 100 units of freeze dried Botulinum toxin A in 5 ml of 1% or 2% Lidocaine with 1:100,000 epinephrine solution (Xylocaine at 1% or 2% with epinephrine 1:100,000, Astra). This resulted in a dosage which is commonly utilized for each of these substances in routine clinical use (20 units Botulinum toxin per ml of 1% or 2% lidocaine with 1:100,000 epinephrine).

In order to assure symmetry and equality of the injections, the sites of injection were predetermined with a template. A predetermined amount and volume of toxin was injected into each location. After the injection, subjects were asked to evaluate the intensity of the pain resulting from the percutaneous injections for both sides of the forehead separately. This was done with a standardized questionnaire approximately 10 minutes after the injection. The pattern of muscular paralysis achieved by the local anesthetic plus Botox was compared to the pattern of paralysis resulting from Botox A alone at one week after the injection. The potency and duration of action of Botox A reconstituted in the vasoconstrictive and anesthetic agent was compared to Botox A reconstituted in 0.9% saline by serial observation until the return of facial muscular function. Subjects were photographed 5–15 minutes after injection, one week after injection, and monthly thereafter attempting maximal forehead muscle contracture.

Two particular examples of such injections are provided. A white female was injected with 20 units Botox in 1 ml 1% lidocaine with 1:100,000 epinephrine in the right side of the forehead and in exactly the same fashion with 20 units Botox, reconstituted in 0.9% saline in the left side of the forehead. A second white female was injected in the same manner, except that 2% lidocaine was used. Eight portions of 0.125 ml were injected into each side of the forehead and the sites of injection were determined by a template. Each subject immediately developed paralysis of the frontalis, procerus, and depressor supercilii muscles on the right side of the forehead. The pattern and extent of immediate muscular paralysis resulting from the immediate action of the local anesthetic drug (Lidocaine 1% or 2%) was predictable of the pattern and extent of delayed paralysis achieved by Botox one week later. The effect of the Botox-induced muscular paralysis faded in a symmetric fashion, indicating that the duration of Botox induced muscular paralysis was not affected by the addition of Lidocaine or epinephrine.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a patient having an acute skin wound, said method comprising locally administering an amount of botulinum toxin in or in close proximity to said acute skin wound, such that healing of said skin wound is enhanced.

2. The method of claim 1, wherein said botulinum toxin is selected from the group consisting of botulinum toxin A, B, C, D, E, F, and G.

3. The method of claim 2, wherein said botulinum toxin is botulinum toxin A.

4. The method of claim 2, wherein said botulinum toxin is botulinum toxin B.

5. The method of claim 1, wherein said administering step is by injection.

6. The method of claim 5, wherein said botulinum toxin is subcutaneously injected.

7. The method of claim 5, wherein said botulinum toxin is intramuscularly injected.

8. The method of claim 5, wherein said botulinum toxin is percutaneously instilled.

9. The method of claim 1, said method further comprising administering a local anesthetic.

10. The method of claim 9, wherein said local anesthetic is lidocaine.

11. The method of claim 9, wherein said local anesthetic is bupivacaine.

12. The method of claim 9, wherein said local anesthetic is mepivacaine.

13. The method of claim 9, wherein said local anesthetic is administered prior to administration of said botilinum toxin.

14. The method of claim 9, wherein said botulinum toxin and local anesthetic are co-administered.

15. The method of claim 1, said method further comprising administering a local vasoconstrictive agent.

16. The method of claim 15, wherein said local vasoconstrictive agent is epinephrine.

17. The method of claim 1, said method further comprising administering a local anesthetic and a vasoconstrictive agent.

18. The method of claim 17, wherein said local anesthetic and said vasoconstrictive agent are administered prior to said botulinum toxin.

19. The method of claim 1, wherein said acute skin wound is a facial wound.

20. The method of claim 1, wherein said acute skin wound is a surgically introduced incision.

21. The method of claim 20, wherein said botulinum toxin is administered prior to making said surgically introduced incision.

22. The method of claim 20, wherein said botulinum toxin is administered while making said surgically introduced incision.

23. The method of claim 20, wherein said botulinum toxin is administered after said surgically introduced incision has been made.

24. The method of claim 1, wherein said acute skin wound is traumatically introduced.

25. The method of claim 1, wherein said acute skin wound is a favorable wound.

26. The method of claim 1, wherein said acute skin wound is an unfavorable wound.

27. The method of claim 1, wherein said acute skin wound comprises subcutaneous tissue.

28. The method of claim 1, wherein said acute skin wound is a head wound.

29. An article of manufacture comprising packaging material and an amount of a botulinum toxin, wherein said packaging material comprises a label that indicates said botulinum toxin is useful for treating a patient having an acute skin wound, and wherein local administration of said amount of said botulinum toxin enhances healing of said skin wound.

30. The article of manufacture of claim 29, wherein said botulinum toxin is botulinum toxin A.

31. The article of manufacture of claim 29, wherein said botulinum toxin is botulinum toxin B.

32. The article of manufacture of claim 29, said article of manufacturing further comprising a local anesthetic.

33. The article of manufacture of claim 29, said article of manufacture further comprising a local vasoconstrictive agent.

34. The article of manufacture of claim 29, said article of manufacture further comprising a local anesthetic and a local vasoconstrictive agent.

* * * * *